(12) United States Patent
Stead et al.

(10) Patent No.: US 6,344,216 B1
(45) Date of Patent: Feb. 5, 2002

(54) CONVERSION OF POWDERED POLYMERS

(75) Inventors: Stanley Gordon Stead, Herts; Peter E. Minister, Leeds, both of (GB)

(73) Assignee: Surfachem Group PLC, Leeds (GB)

( * ) Notice: Subject to any disclaimer, the term of this patent is extended or adjusted under 35 U.S.C. 154(b) by 0 days.

(21) Appl. No.: 09/226,945

(22) Filed: Jan. 8, 1999

Related U.S. Application Data

(63) Continuation of application No. 08/335,786, filed on Feb. 17, 1995, now Pat. No. 5,858,406, which is a continuation-in-part of application No. 08/170,268, filed on Dec. 29, 1993, now Pat. No. 5,496,891, which is a continuation-in-part of application No. PCT/GB92/00842, filed on May 11, 1992.

(51) Int. Cl.[7] .............................. A61K 9/14; A61K 9/16; A61K 9/20; A61K 7/00; A61K 7/02
(52) U.S. Cl. ..................... 424/464; 424/401; 424/465; 424/470; 424/489; 514/944; 514/951
(58) Field of Search ................................ 424/464, 465, 424/489, 401, 470

(56) References Cited

U.S. PATENT DOCUMENTS 4,386,120 A * 5/1983 Sato et al. .................. 427/213
4,826,880 A * 5/1989 Lesniak et al. ............... 521/53

* cited by examiner

Primary Examiner—James M. Spear
(74) Attorney, Agent, or Firm—Rohm & Monsanto, PLC

(57) ABSTRACT

Carbomer or cross-polyacrylate polymers which are conventionally provided in a powdered form are converted to a granulated, pelletized or tablet form for subsequent use, in combination with a liquid medium, to form a gel from which products such as liquid detergents, cosmetics and toiletries can be produced. Conversion of the polymer into a granular, pelletized or tablet form has been demonstrated to improve handling of the dry polymer, thereby mitigating against many of the problems incurred with the use of conventional powders, as well as to improve the rate of blending of the polymer with a liquid medium. In some embodiments, the polymer is blended with an electrolyte which may be a salt, acid or acid salt having a pK which is at least 1 unit, and preferably 2 units, greater than the pK of the polymer.

15 Claims, 1 Drawing Sheet

CONVERSION OF POWDERED POLYMERS

CROSS REFERENCE TO RELATED APPLICATION(S)

This application is a continuation application of U.S. Ser. No. 08/335,786 filed on Feb. 17, 1995, now U.S. Pat. No. 5,858,406 issued on Jan. 12, 1999. U.S. Ser. No. 08/335,786 is a continuation-in-part of co-pending International Application Ser. No. PCT/GB92/00842 filed on May 11, 1992 and designating the U.S. Ser. No. PCT/GB92/00842 entered the national stage in the United States on Dec. 29, 1993 and was assigned U.S. Ser. No. 08/170,268 Dec. 29, 1993 and has now issued as U.S. Pat. No. 5,496,891 on Mar. 5, 1996.

The present invention relates to carboxylic acid polymer compositions and particularly relates to concentrates of acrylic acid polymers and their use to prepare gels of diluted and neutralized polymer.

The polymers to which the invention relates include cross-linked polymers of acrylic acids which are widely used as thickeners, stabilizers and emulsifiers in many industries. Said cross-linked polyacrylic acids are produced and sold under a number of trade names for example Carbopol (B F Goodrich), Acrisint (Sigma), Pemulen (B F Goodrich), Junlon (Nihon Kogakyu) etc. They are however most often referred to by either of the generic terms carbomer and cross-polyacrylate, (developed by the Cosmetics, Toiletries or Fragrances Association). The polymer products are referred to by these names in this application.

Said products so described are supplied in the form of very fine powders with poor flow properties, and handling of these products is not easy. However, it has always been considered that the products must be in the form of very fine powder if complete wetting and reasonably rapid hydration of each particle is to take place when the products are added to a liquid medium, such as water, to form a gel from which products such as liquid detergents, cosmetics, toiletries or pharmaceutical products can be made. A consequence of the products being in the form of a very fine powder is that they have a pronounced tendency to dust and fly about the work place even when care is taken to minimise this.

It is conventionally regarded therefore that, despite the handling difficulties, the products must be supplied in the form of fine powders since, when they are to be converted to a gel, and in the initial stage of hydration for this conversion i.e., wetting of the powders, the formation of a very stiff gel on the outside of the powder particles occurs which delays and restricts the entry of further water to hydrate the remainder of the particle. The stiff gel on the outside of the particle therefore tends to prevent further water ingress into the particle, thereby retarding the formation of a smooth gel. In addition, agglomerates of the powder particles form lumps which increases the problem of wetting out and dispersion.

Furthermore, when disturbed, the dry powder tends to develop strong electrostatic charges which impairs further the ability of the powder to flow in the required direction and, in the extreme, causes small agglomerates to fly about which results in loss of material. This makes the automatic measuring out of the carbomers virtually impossible.

As a result of these problems, manufacturers of the products always advise that the said product be carefully sifted into the water in an attempt to break up the dry agglomerates which tend to form during storage. Furthermore, these carbomers, when fully swollen and hydrated, have the property of suspending insoluble gases, liquids and solids. This property, although very desirable in most instances, can make the removal of air bubbles from the mixture very difficult, if not impossible, within a reasonable period of time.

In an attempt to overcome this problem it has been proposed to prepare concentrated dispersions of resins in water. However, due to the high viscosity of said resins, they are extremely difficult or impossible to handle. A further initiative, as described in co-pending application No 9114095.4 provides, by incorporating small proportions of salts of multi-valent cations in these dispersions either by dry blending the polymer and salt together before adding them to the water, or by mixing the salt, powdered carbomer, and water in any order, a concentrate which has been found to be extremely effective and to have gained acceptance as a workable alternative.

The provision of said multi-valent cations in the blend has been found to be acceptable but further research has shown that the important factor of handling difficulties of the powdered carbomer in a dry state is not properly addressed. The addition of additional matter to the carbomer, although having an important effect on the characteristics of the carbomer, does not solve many of the other inherent handling problems of the carbomer, and also meets resistance from users reluctant to change to a product which requires new certification and approval. For example, the form in which the carbomer is provided is important in allowing improvements both in the mixing of the carbomer in a liquid medium to form the gel and also in improving the storage characteristics of the carbomer.

The aim of the present invention therefore is to provide an improvement in the form in which a polymer is provided such that the ease of mixing or blending of the polymer in a liquid medium to form a gel is improved in relation to existing powdered polymers and the polymer in its improved form is non-dusting, non-static and has improved flow-characteristics.

The present invention provides for the conversion of a powdered polymer wherein said polymer is converted to a granular, pelletised or tablet form.

Typically said polymer will be a powdered carbomer or cross polyacrylate and will, in a first embodiment, be comprised wholly of carbomer, or cross-polyacrylate.

The carbomer in its converted form will be capable of rapid dispersion when added to a liquid medium to form a gel substance.

In a second embodiment, the polymer will comprise a carbomer or cross-polyacrylate with which is blended an electrolyte to form a composition which is subsequently converted to a granular, pelletised, or tablet form.

Typically said electrolyte will have any of the following characteristics, namely it is;
  readily soluble in liquid,
  an acid or salt or acid salt of mono-or poly-valent cations or combinations thereof,
  a salt, acid or acid salt, whose pK value is at least 0.5 units and preferably 1.0 unit, less than the pK value of the carbomer itself which is typically 4.3,
  preferably solid and non-volatile at normal temperatures,
  preferably non-toxic,
  stable under normal storage conditions and preferably does not discolour, polymerise or change in any other way.

Typically, said electrolyte will also be non-hygroscopic.

When said electrolyte is an acid, or an acid salt, the pK value of the acid, a measure of its acidity, will, be at least equal to, and preferably 1.0 unit less than the pK value of the carbomer.

Preferably, the pK value of the acid will be 2.0 units less than the pK value of the carbomer, which typically has a pK value of 4.3.

In a further aspect of the invention, the electrolyte used in a blended form with the carbomer, will be an acid salt of mono-valent or multivalent cations.

Typically said blend will be easily granulated or pelletised and will be supplied in that form. To form said pellets, tablets, or granules into the required gel will require the conventional addition and mixing with a liquid medium followed by neutralisation of the mixture. Typically said liquid medium will be water but may also be any of an organic solvent such as ethanol, propylene glycol or a blend of a polar hydroxylic solvent and a non-swelling solvent.

Preferably, the polymer will be provided in a granular form. Typically to form granular products, either wet or dry granulation methods can be employed. Dry granulation involves the use of high pressure to force the particles into contact with each other and can be carried out either in moulds by means of a ram or by forcing the powder through a screen with rollers. Subsequently the material may be reduced in size and put through screens to enable a selected size range to be obtained. Wet granulation typically involves treatment with a small proportion of water to assist binding of the particles which then occurs without the need for high pressures. Other solvents can be used, but in this instance would be considered undesirable. Drying of the granular material may also be carried out as part of the process.

Conventionally it is generally held that for materials of the type of this invention, small particle size is essential if the rate of hydration of the said materials is to be acceptably short, hence the provision of the carbomer in powder form. This has to date, prevented the use of larger particle sizes as the rate of hydration has hitherto been deemed to too slow to be economically or practically possible. The provision of carbomer in granular, tablet or pellet form is in effect contrary to the conventional wisdom as it increases the size of the carbomer parts to be mixed, but unexpectedly achieves significant improvements.

The improvement of the mixing of the granules with the liquid medium is possibly due to the reduction of air held in the mixture allowing the quicker addition of the granules and dispersion of same.

A further, decreased degree of swelling of the composition is shown, by this invention, by optionally adding small proportions of electrolyte when the polymer is in its acid form. It is shown that only a small fraction of the amount of electrolyte required to reduce viscosity of the neutralized form of the polymers is needed to achieve the same effect in the acid form. The invention therefore provides a means of adding said electrolytes to the said polymer when the polymer is in the acidic form prior to neutralization. The fraction of the electrolyte required is so small that a reduction of viscosity of the neutralized form is less than the experimental error in measuring same and hence can be disregarded.

It has been found that the main advantages are in the handling of the polymer and at the same time improving the mixing characteristic of the polymer during hydration.

The original carbomer or cross-polyacrylate which is supplied in a powder form is necessarily of low bulk density, generally between 200 and 250 kg per cubic meter wherein the granulated product of the invention has a notably greater bulk density up to 600 kg per cubic meter hence providing considerable saving in terms of a reduced cost of packaging and storage.

A main advantage of the granulate or pellets of the invention is that by granulating or pelletising the mixture then the drawbacks of the original powders previously discussed are overcome in that the granules, pellets or tablets of the invention are non-dusting and do not develop static charges. A further advantage is that the granules flow very readily and disperse, even when rapidly added to stirred water without the disadvantage of clumping occuring. Furthermore, when required, the viscosity of the acidic gel can be reduced with the addition of the electrolytes into the carbomer and subsequently granulating the composition and hence the requirement to remove any unhydrated material by a stirring process is greatly reduced. Providing the said material in the form of granules or pellets, either with or without electrolyte additives, allows the materials to be used with automatic weighing systems hence improving the efficiency of handling of the material in comparison to those products which are currently available.

Examples comparing the effect of granulating carbomers in relation to the conventional powder are now discussed.

EXAMPLE 1

Carbopol 980 (BF Goodrich & Co Product) was compressed in a standard tablet press to give tablets with a diameter of 2.9 cm width and 0.8 cm depth. The tablets were carefully crushed and sieved to remove any fines and over-size particles. The resulting granulate, with a particle size between 0.2 and 0.6 mm flowed readily and evenly, did not clump together on shaking or stirring, and was free from a tendency to dust. On being rapidly added to 100 times its own weight of stirred distilled water, the particles dispersed readily and became fully hydrated within 30–60 minutes to give a translucent viscous mucilage which retained much of the air entrained within it during the mixing.

Comparison mixtures were prepared from the same batch of Carbopol 980 using conventional techniques as follows:
  a) by adding the powder carefully to the distilled water to avoid lumping as the powder came into contact with the water. Some dusting of the powder was noted. The time taken for the powder to hydrate fully was again between 30 and 60 minutes and a similar mucilage resulted as that described above.
  b) the powder was added at the same rate as the granulate. More dusting was observed and a number of large agglomerates were formed. These took many hours to fully wet out and hydrate. When the hydration was complete the mucilage was similar to that produced by method (a) above.

EXAMPLE 2

100 g of Carbomer 940 in a rotating plate granulator was sprayed with water until agglomeration started. Approximately 6 ml was needed to reach this point, the process was continued until the particle size had increased to about 1 mm. The resulting granules were free-flowing and non-dusting. When added rapidly to stirred demineralised water, they rapidly dispersed and then hydrated within approximately 30 minutes to give a viscous translucent mucilage.

The examples given above clearly indicate that the granulation of the carbomer allows the carbomer to be added to the water at faster flows, at a more economic flow rate whilst ensuring that a usable mucilage is obtained. This faster flow rate is achieved by the granulation of the carbomer and the end result can only be equalled using conventional carbomers if the carbomer powder is added extremely slowly in an attempt to prevent lumping occuring. Attempts to add the powder at the same rate as the granules results in a substandard mucilage being produced.

Further advantages are obtained in that the dusting problem experienced using conventional techniques is eliminated by granulation and the health and safety problems associated therewith are eliminated.

Additionally, small levels of electrolytes may be added to improve further the mixing characteristic of the granules, pellets or tablets with the liquid medium form the gel and the following are examples using this process.

EXAMPLE 3

100 grams of Carbopol 940, a fine powder with a particle size range of about 1 to 5 microns, was placed in a rotating plate wet granulator and the machine switched on. There was gradually added 10 ml of a 20% w/v solution of magnesium sulphate heptahydrate by spraying. The liquid was rapidly absorbed by the Carbopol and the mixture became granular within a short time, the granular product was then removed and passed through a sieve having 12 mesh openings/linear inch. 2.5 grams of the material which passed through the sieve was very rapidly added to a beaker containing 500 ml of distilled water of room temperature while it was being stirred. The granules immediately dispersed without lumping together and over 30 minutes swelled to give a homogeneous low viscosity hazy solution which rapidly de-aerated when the stirrer was switched off. Sodium hydroxide solution was added to this solution until a stable pH value of 7.2 was reached. The viscosity, measured on a Brookfield RVT viscometer at 20 rpm, of the brilliantly clear bubble-free gel was 46000 cps.

For comparison purposes a 0.5% solution of the same batch of Carbopol 940 was made directly from the powder using the same technique. The powder was rapidly tipped into the water whereupon severe lumping occurred and these lumps took several hours to fully hydrate to give a homogeneous mix. This solution did not allow the air entrained to rise out when stirring was stopped and when brought to a pH value of 7.2 contained many bubbles although it was otherwise as clear as the sample made from the granulated form. The viscosity measured in the same manner as before was 49000 cps

EXAMPLE 4

Similarly a sample of Carbopol 940 was dry blended with 2% of its weight of desiccated sodium sulphate, and dry granulated by compression. The coarse product was sieved to remove fines and particles larger than 10 mesh, and the rejected material was returned for further working. The residual material was then tested.

|  | Viscosity cps | |
| --- | --- | --- |
|  | Carbopol only | Carbopol/sodium sulphate blend |
| 1% Carbopol 940 un-neutralised | 960 | 3 |
| 1% Carbopol 940 neutralised pH 7.2 | 57000 | 55000 |

The viscosity of the un-neutralised Carbopol was nearly the same as water and since it did not exhibit any significant yield value the air which had been entrained in the solution rapidly rose to the surface so that upon neutralisation the gel formed was completely free of air bubbles.

EXAMPLE 5

A further trial using 0.8% magnesium sulphate in place of the sodium sulphate and the same batch of Carbopol 940 gave:

| Viscosity un-neutralised cps | 4 |
| --- | --- |
| Viscosity after neutralisation | 56000 |

EXAMPLE 6

Blends of Carbopol 940 with 8% malic acid, and 0.6% sulphamic acid were prepared and gave:

|  | No addition | 0.67% sulphamic acid | 8.0% malic acid |
| --- | --- | --- | --- |
| Viscosity un-neutralised cps | 960 | 4 | 5 |
| Viscosity neutralised | 57000 | 56000 | 40000 |

It is clear that the increased addition of malic acid needed to reach the low un-neutralised viscosity has raised the overall electrolyte level to a point where a marked loss of viscosity has occurred after neutralisation, whereas there is virtually no loss of viscosity in the sample in which sulphamic acid was used. Because the malic acid, pK=3.4, is a much weaker acid than sulphanic acid (pK=1.92), much more is needed to effect the reduction in viscosity of the un-neutralised dispersion.

Other suitable acids include

Benzene-sulphonic acid

Citric acid cyclo-propane-1,1-di-carboxylic acid tartaric acid however this listing is not intended to be exhaustive.

From these examples, it can be clearly seen that the addition of an electrolyte to the carbomer, provides an acidic dispersion which has a lower viscosity and hence can again be granulated, pelletised or formed into tablets and supplied to the users in that form whilst maintaining an adequate rate of hydration comparable with the powders currently available. The addition of the said electrolyte to the carbomer in the acid form, as opposed to after neutralisation, is inventive and novel in its own right. The proportion of said electrolyte should not be so high as to seriously reduce the viscosity of the neutralised gel formed by dispersion of the granulate in water and adding sufficient alkali to reach the required pH value which will normally be in the range of 5.0–8.5 but may for specific purposes be outside this range. It is also envisaged that the controlled addition of acid over and above that needed to achieve the effect of reducing the viscosity of the un-neutralised dispersion can be used as a means of reducing the batch to batch variation of these polymers when neutralised and, furthermore, to bring said batches which have a viscosity above the specified limit into specification. A further aspect of the invention therefore allows the manufacturer or user of the material to adjust and take into account any variation which may occur in the un-neutralised dispersion when hydrated.

It is known that the viscosity of carbomer dispersions in the acid form can be reduced in viscosity by the addition of acid in small proportion and hydrochloric acid and phosphoric acid have been suggested. Blending with the carbomer before addition to the water is a novel concept and the suggested acids would obviously be totally unsuitable in any case. Addition of electrolytes in the specific form of sodium salt of ethylene diamine-terra-acetic acid has also been recommended for controlling the viscosity of finished products by addition at the end of the process.

A specific embodiment of an industrial granulation technique to form the granules of the invention is now described with reference to the accompanying drawings wherein;

BRIEF DESCRIPTION OF THE DRAWING

Referring to FIG. 1, the apparatus comprises a carbomer supply means 2, a carbomer feed means 4, pressurised rollers 6, and two granulating sieves 8 and 10.

Figure 1:
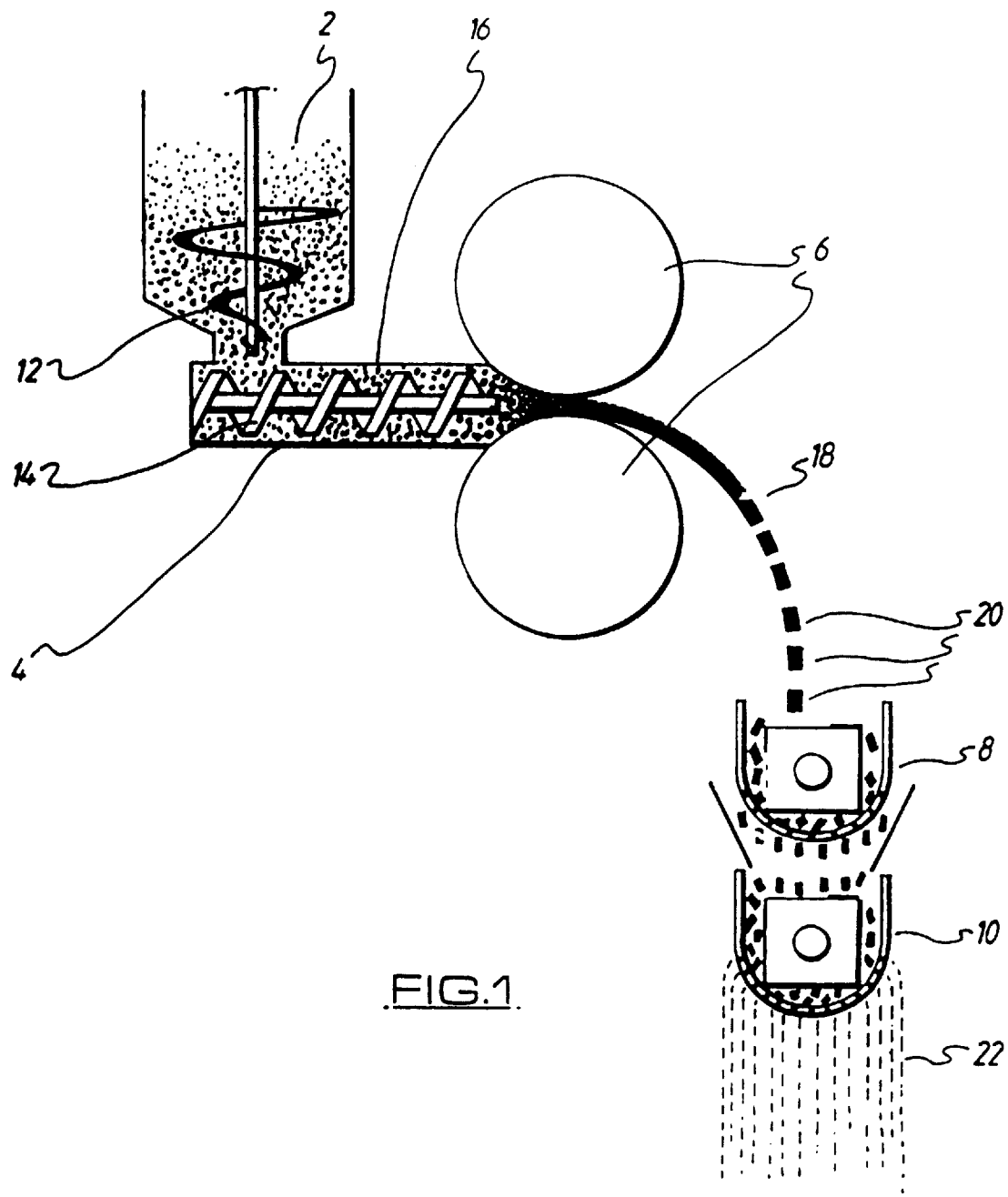
FIG. 1 illustrates, a simplified partially schematic representation of an apparatus useful in the granule forming process.

The supply means 2 are provided to supply through gravity augmented by a spiral drive 12 carbomer powder into the feed means. The spiral drive is provided to prevent bridging of the carbomer powder and to ensure that the powder will enter the feed means.

The feed means 4 comprises a plurality of powered augers 14 which act to move the powder horizontally along cylinder 16 to the pressurised rollers 6. As the powder passes through the rollers the powder is compressed together into a flake 18 which subsequently breaks into smaller fragments 20 as it enters the first granulating sieve 8. Provided adjacent each of the sieves is a rotating means with arms which cause the flake to be forced through the first sieve 8 into the second sieve 10 where the action is repeated and granules 22 of the required size are deposited into a granule hopper (not shown). Typically the mesh size of the first sieve 8 will be larger than that of the second sieve to allow a staggered reduction in the granule dimension to the dimension required.

Typically to form said granules, pellets or tablets into the required gel, will require the addition of a liquid form which will typically be water but may also be an organic solvent such as ethanol, propylene glycol or a blend of a polar hydroxylic solvent and a non-swelling solvent.

It is generally held that carbomers of the type so described have inherent problems in that static charges develop and dusting occurs when said carbomers are provided in powder form. These problems have been accepted by the industry as being unavoidable due to the need to use carbomer in the powder from. This need has been based on the belief that small particle size of the carbomer is essential in order to obtain an economical rate of hydration. Particles of greater size, it has been believed, or the loose agglomerates formed on storage and by inter-particle attraction lead to a rate of hydration which is deemed to be too long to be economically or practically possible. The invention shows that this belief is incorrect.

The current invention, by providing the carbomer in a granulate, pellet or tablet condition eliminates the dusting problem and greatly reduces the static charge development between particles yet has been found also improve the rate of hydration or mixing characteristic of the polymer. These advantages are considerable in that handling of the carbomer and all the associated problems therewith is greatly improved whilst at the same time the dispersion of the carbomer when forming into a gel is not adversely affected. This is in complete contrast to the currently conventional belief.

What is claimed is:

1. A powdered carbomer or cross-polyacrylate polymer of the type used to form a gel when added to a liquid medium and neutralised wherein said powdered carbomer or cross-polyacrylate polymer is provided in a granular, pelletised, or tablet form having a particles size of at least 200 microns prior to addition to the liquid medium.

2. A powdered carbomer or cross-polyacrylate polymer according to claim 1, wherein the powdered carbomer or cross-polyacrylate polymer is in a granular form.

3. A polymer according to claim 2 wherein the polymer is a cross-polyacrylate.

4. A method of forming a powdered carbomer or cross-polyacrylate polymer of the type used to form a gel when added to a liquid medium into a suitable form for formation into a gel and, wherein prior to using the polymer to form a gel, the method comprises the step of:

converting the powdered carbomer or cross-polyacrylate polymer to a granular, pelletised or tablet form having a particles size of at least 200 microns.

5. The method of claim 4, wherein the step of converting comprises granulating.

6. The method of claim 5 wherein the step of granulating includes the steps of:

compressing the powdered carbomer or cross-polyacrylate polymer to form a flake; and breaking the flake into granules of a predetermined size by passing the flake through at least one sieve.

7. The method of claim 5 wherein the step of granulating comprises wet granulating.

8. The method of claim 7 wherein wet granulating comprises the steps of:

adding a liquid which is capable of swelling the powdered carbomer or cross-polyacrylate polymer to the powdered polymer in an amount sufficient to bind the powder into particles; and drying the bound particles to form granules.

9. The method of claim 4 comprising the further step of, prior to said step of converting, blending an electrolyte with the powdered carbomer or cross-polyacrylate.

10. The method of claims 4 or 9 wherein the granular, pelletised or tablet form carbomer or cross-polyacrylate polymer is added to a liquid medium to form a gel.

11. The method of claim 10 further including the step of:

formulating the resulting gel into a liquid detergent, cosmetic, toiletry, or pharmaceutical.

12. A method of forming a powdered carbomer or cross-polyacrylate polymer into a suitable form for formation into a gel and, wherein prior to using the polymer to form a gel, the method comprises the steps of:

compressing the powdered carbomer or cross-polyacrylate polymer to form a flake; and breaking the flake into granules of a predetermined size by passing the flake through at least one sieve.

13. The method of claim 12 comprising the further step of:

adding the granules of carbomer or cross-polyacrylate polymer to a liquid medium.

14. The method of claim 13 further including the step of:

formulating the resulting gel into a liquid detergent, cosmetic, toiletry, or pharmaceutical.

15. The method of claim 12 comprising the further step of, prior to said step of compressing, blending an electrolyte with the powdered carbomer or cross-polyacrylate.

* * * * *